(12) United States Patent
Anderson et al.

(10) Patent No.: US 12,208,047 B2
(45) Date of Patent: *Jan. 28, 2025

(54) METHOD AND APPARATUS FOR DERMATOLOGICAL TREATMENT

(71) Applicant: The General Hospital Corporation, Boston, MA (US)

(72) Inventors: Richard R. Anderson, Boston, MA (US); Mathew Avram, Boston, MA (US); Fernanda H. Sakamoto, Boston, MA (US); Wikunda Limpiangkanan, Cambridge, MA (US); William A. Farinelli, Danvers, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/482,247

(22) Filed: Oct. 6, 2023

(65) Prior Publication Data

US 2024/0299229 A1    Sep. 12, 2024

Related U.S. Application Data

(63) Continuation of application No. 17/226,889, filed on Apr. 9, 2021, now Pat. No. 11,813,218, which is a
(Continued)

(51) Int. Cl.
*A61H 1/00*    (2006.01)
*A61B 17/00*   (2006.01)
(Continued)

(52) U.S. Cl.
CPC ........ *A61H 1/008* (2013.01); *A61B 17/0466* (2013.01); *A61B 17/06166* (2013.01);
(Continued)

(58) Field of Classification Search
CPC ................ A61H 1/008; A61B 17/0466; A61B 17/06166; A61B 17/064; A61B 17/0644;
(Continued)

(56) References Cited

U.S. PATENT DOCUMENTS 6,178,346 B1    1/2001    Amundson et al.
7,429,258 B2    9/2008    Angel et al.
(Continued)

FOREIGN PATENT DOCUMENTS

CN    101563113 A    10/2009
CN    102119006 A    7/2011
(Continued)

OTHER PUBLICATIONS

PCT International Search Report and Written Opinion, PCT/US2013/049445, Oct. 18, 2013.
(Continued)

*Primary Examiner* — Jonathan T Kuo
(74) *Attorney, Agent, or Firm* — Quarles & Brady LLP (57) ABSTRACT

Exemplary methods and systems can be provided for resurfacing of skin that include formation of a plurality of small holes, e.g., having widths greater than about 0.2 mm and less than about 0.7 mm or 0.5 mm, using a mechanical apparatus. Compressive and/or tensile forces can then be applied to the treated region of skin as the damage heals to facilitate hole closure, and provide enhanced and/or directional shrinkage of the treated skin area.

20 Claims, 8 Drawing Sheets

Related U.S. Application Data continuation of application No. 15/678,959, filed on Aug. 16, 2017, now abandoned, which is a continuation of application No. 14/412,079, filed as application No. PCT/US2013/049445 on Jul. 5, 2013, now abandoned.

(60) Provisional application No. 61/668,744, filed on Jul. 6, 2012.

(51) Int. Cl.
  *A61B 17/04* (2006.01)
  *A61B 17/06* (2006.01)
  *A61B 17/064* (2006.01)
  *A61B 17/08* (2006.01)
  *A61B 17/20* (2006.01)
  *A61B 17/34* (2006.01)
  *A61K 8/02* (2006.01)
  *A61L 24/00* (2006.01)
  *A61Q 19/08* (2006.01)

(52) U.S. Cl.
  CPC ........ *A61B 17/064* (2013.01); *A61B 17/0644* (2013.01); *A61B 17/083* (2013.01); *A61B 17/34* (2013.01); *A61K 8/0208* (2013.01); *A61L 24/001* (2013.01); *A61Q 19/08* (2013.01); *A61B 2017/005* (2013.01); *A61B 2017/00747* (2013.01); *A61B 2017/00761* (2013.01); *A61B 2017/00792* (2013.01); *A61B 2017/0645* (2013.01); *A61B 17/205* (2013.01); *A61K 2800/95* (2013.01)

(58) Field of Classification Search
  CPC ..... A61B 17/083; A61B 17/34; A61B 17/205; A61B 2017/005; A61B 2017/00747; A61B 2017/00761; A61B 2017/00792; A61B 2017/0645; A61K 8/0208; A61K 2800/95; A61L 24/001; A61Q 19/08
  See application file for complete search history.

(56) References Cited

U.S. PATENT DOCUMENTS

| | | | |
|---|---|---|---|
| 7,500,963 B2 | 3/2009 | Westbye et al. | |
| 7,850,683 B2 | 12/2010 | Elkins et al. | |
| 2003/0083645 A1 | 5/2003 | Angel et al. | |
| 2003/0135161 A1 | 7/2003 | Fleming et al. | |
| 2003/0163160 A1 | 8/2003 | O'Malley et al. | |
| 2005/0020979 A1 | 1/2005 | Westbye et al. | |
| 2005/0283141 A1 | 12/2005 | Giovannoli | |
| 2006/0193819 A1 | 8/2006 | Lu | |
| 2007/0167958 A1 | 7/2007 | Sulamanidze et al. | |
| 2008/0033334 A1 | 2/2008 | Gurtner et al. | |
| 2008/0183164 A1 | 7/2008 | Elkins et al. | |
| 2008/0306471 A1 | 12/2008 | Altshuler et al. | |
| 2011/0028898 A1 | 2/2011 | Clark, III et al. | |
| 2012/0158100 A1 | 6/2012 | Schomacker | |
| 2012/0226214 A1 | 9/2012 | Gurtner et al. | |
| 2012/0226268 A1 | 9/2012 | Liu et al. | |
| 2013/0204238 A1 | 8/2013 | Lederman et al. | |
| 2014/0039523 A1 | 2/2014 | Austen | |
| 2016/0095592 A1 | 4/2016 | Levinson et al. | |

FOREIGN PATENT DOCUMENTS

| | | |
|---|---|---|
| CN | 102143724 A | 8/2011 |
| CN | 102178616 A | 9/2011 |
| CN | 202113484 U | 1/2012 |
| CN | 103547226 A | 1/2014 |
| EP | 1618925 A1 | 1/2006 |
| EP | 2181732 A1 | 5/2010 |
| JP | 2003532480 A | 11/2003 |
| JP | 2009545382 A | 12/2009 |
| RU | 61559 U1 | 3/2007 |
| RU | 2325859 C2 | 6/2008 |
| TW | 200841866 A | 11/2008 |
| WO | 2007066339 A1 | 6/2007 |
| WO | 2008052189 A2 | 5/2008 |
| WO | 2009040493 A1 | 4/2009 |
| WO | 2009072711 A2 | 6/2009 |
| WO | 2011104875 A1 | 9/2011 |
| WO | 2011140497 A2 | 11/2011 |
| WO | 2012103492 A1 | 8/2012 |
| WO | 2014008481 A1 | 1/2014 |

OTHER PUBLICATIONS

European Patent Office, Supplementary European Search Report, Application No. EP13813955.5, Mar. 18, 2016.
Taiwan Intellectual Property Office, Search Report, Application No. 102124230, Sep. 2, 2016.
China National Intellectual Property Administration. First Office Action for application 201810128503.5. Mailed on Mar. 26, 2020. With Translation.
Korean Intellectual Property Office. Office Action dated Feb. 20, 2020. With translation.

METHOD AND APPARATUS FOR DERMATOLOGICAL TREATMENT

CROSS-REFERENCE TO RELATED APPLICATIONS

This application is a continuation of U.S. patent application Ser. No. 17/226,889 filed on Apr. 9, 2021, which is a continuation of U.S. patent application Ser. No. 15/678,959 filed on Aug. 16, 2017, which is a continuation of U.S. patent application Ser. No. 14/412,079 filed on Dec. 30, 2014, which represents the national stage entry of PCT International Application No. PCT/US2013/049445 filed Jul. 5, 2013, which claims the benefit of U.S. Provisional Patent Application Ser. No. 61/668,744, filed Jul. 6, 2012, all of which are incorporated herein by reference for all purposes.

TECHNICAL FIELD

The present disclosure relates to cosmetic methods and systems for improved fractional resurfacing of skin tissue and similar procedures, specifically, such methods and systems that facilitate enhanced and/or directional reduction in skin area or reduction of wrinkles.

BACKGROUND

There is an increasing demand for repair of or improvement to skin defects, which can be induced by aging, sun exposure, dermatological diseases, trauma, surgical procedures, heredity, and the like. Skin loses its tone and smooth texture as it ages, commonly developing wrinkles and laxity. This can be further compounded by photodamage and other effects such as, e.g., scarring from trauma, age-related rhytides, and striae. Aged skin is characterized by a flattened dermal-epidermal junction, thinning epidermis and dermis, less fibrous collagen, and alterations in elastin organization. Skin rejuvenation therapies work to remove these damaged tissues and/or and stimulate the growth of new, healthy collagen, elastic fibers and skin cells and thereby improve the appearance of the skin.

Reduction in the appearance of wrinkles is an objective of many dermatological procedures and treatments. For example, a face lift operation is a standard surgical procedure in which skin is removed from in front or behind the ears, which pulls and lifts adjacent skin from the face and neck that has sagged during aging. However, the result of this procedure is often an unnatural stretched appearance. If skin on the face or neck itself could be removed in a way that decreases the area of skin, with preference to one or more given directions for reduction of skin area, and without visible scarring, the result would be a more natural appearance while still removing unwanted sagging or redundant skin.

Certain treatments may be used to improve skin defects by irradiating the skirt with electromagnetic energy, which, can lead to beneficial responses to improve tile treated skin condition. A common procedure for skin rejuvenation, i.e., laser resurfacing, uses light, energy to heat and damage the upper dermis. However, laser resurfacing has a poor side effect profile, with many patients experiencing prolonged erythema, scarring and dyspigmentation.

Recently, the development and use of fractional skin therapy has achieved better results. Fractional damage can include forming small regions of damage in tissue (e.g., ablation or thermal damage) that are surrounded by healthy tissue. A small size of the damaged regions (e.g., generally less than, about 1 mm) and proximity of healthy tissue can facilitate a rapid healing of the damaged regions, as well as other desirable effects such as tissue shrinkage. Laser-based fractional resurfacing techniques and devices involve the use of expensive and potentially dangerous lasers or other sources of intense optical energy to damaged tissue. Such optical systems can be expensive, present safety hazards, and require a skilled physician or clinician for their operation. Further, fractional resurfacing treatments tend to produce general tightening of the skin that has no directional preference or bias.

However, many wrinkles tend to present on certain parts of the body with a general orientation, such as wrinkles extending laterally from the corners of the eyes or month, or along the neck beneath the jaw. Directional shrinkage of skin can be achieved by removing elongated areas of skin in an appropriate shape, and then joining the edges of remaining skin (e.g. with sutures) to "pull" the skin back; in a particular direction. Such procedures, as used in conventional facelifts, create large scars that must be carefully located, and may generate some unnatural-looking shrinkage in response to the large-scale removal and repositioning of the skin.

It has been proposed to remove smaller portions of skin, e.g. on the order of a few millimeters wide, and to close the resulting holes with sutures or the like to produce a more controlled reduction of skin area. Such holes should be elongated (e.g. lenticular or elliptical in shape) to facilitate their closure by approximating their longer edges and avoid the formation of dog-ears when they are collapsed. However, such holes are still large enough to produce visible markings when healed, and foil healing time may require up to a few weeks. Further, closure of such holes is a skill-intensive procedure that would require manipulation such as individual suturing or manual, even approximation followed by application of an adhesive coating such as a cyanoacrylate adhesive to keep the holes closed until they heal. Such hole closure procedures would be time-intensive and prone to visible scarring.

Accordingly, there may be a need for a relatively simple, inexpensive, robust and safe cosmetic method and system that can be mechanical in nature, and would overcome at least some of such exemplary deficiencies described above, and that can be configured to produce fractional damage in biological tissue that leads to directional reduction of skin surface area without causing visible scarring.

SUMMARY

The present disclosure relates to exemplary embodiments of simple, inexpensive, and safe cosmetic methods and systems for mechanical generation of a plurality of small holes, e.g., microregions of damage, in biological tissue, such as skin, and for manipulating the treated skin to generate a cosmetically desirable reduction of skin area that can be enhanced and/or that has a particular or preferred direction. Such exemplary boles can have a width or diameter that is, e.g., between about 0.2 mm and 0.7 mm, or preferably between about 0.2 mm and 0.5 mm as measured along the tissue surface. Such holes can extend into or preferably through the entire thickness of the dermis. The fractional area of skin removed by formation of such holes in a treatment region can be between about 5% and 50%, or between about 10% and 30%. Formation of holes in this sub-millimeter size range and areal coverage is well-tolerated by the body, with, minimal risk of scarring, infection, or other complications.

An exemplary embodiment of a cosmetic method according to the present disclosure can be provided that can include a formation of a plurality of holes in a region of skin as described above, and then an application of tensile and/or compressive stresses in a direction generally along the surface of the skin to the treated region during subsequent healing process. Such stresses can enhance overall reduction in the treated region and/or provide a directional bias to the resulting shrinkage. The applied stresses can be maintained in the treated region until the holes have substantially closed and/or tissue regrowth has been effectively modified, e.g., between about 4-6 days or longer. In certain exemplary embodiments, this time period may be much shorter, e.g., on the order of several minutes or hours, if a tissue adhesive, glue, or the like is used to facilitate hole closure.

In one exemplary embodiment a pre-stretched or heat-shrinkable film can be adhered to the surface of the treated region after the holes are formed. The resulting compressive stresses can enhance hole closure in the direction of the applied stresses and/or affect the orientation of collagen or other structures that grow or evolve as part of a healing response in the tissue surrounding the small holes. A rigid film, plate, or other object can optionally be adhered over the stretched film to provide mechanical stability and maintain deformation of the treated region during the primary healing process.

In further exemplary embodiments, compressive stresses can be generated in the treated region of akin by applying one or more surgical staples and/or sutures to the area. The staples and/or sutures are preferably large, such that they span several of the formed holes, and optionally the entire treated region. In certain embodiments, a plurality of staples or sutures can be applied to a single area at different orientations, to provide omnidirectional compressive stresses that can enhance hole closure and overall shrinkage of the treated region as compared to a similarly-treated region without the applied stresses.

In other exemplary embodiments, compressive stresses can be generated by applying a shrinkable material to the skin surface after the holes are formed therein. The shrinkable material can include, e.g., a heat-shrink film adhered to the skin surface and then heated, a liquid layer that can polymerize or react to form an adherent film that reduces in size as it forms, cures or ages, etc.

In other exemplary embodiments, a photoactivated adhesive can be applied to the surface of the treated region, and a compressive or tensile stress can be generated in the region, while directing a light energy onto the region to activate the adhesive. The photoactivated adhesive can include, e.g., rose bengal or any other photoactivated biological adhesive known in the art.

In still further exemplary embodiments, tensile stresses can be generated in the treated region of skin, by stretching the treated region in one or more directions along the skin surface, which can facilitate hole closure and shrinkage in a direction orthogonal to the direction of the applied tensile stress. Such tensile stresses can be manually generated and then maintained, e.g., by adhering a rigid film, plate, or other object to the stretched area of skin.

According to further exemplary embodiments of the present disclosure, a system can be provided for generating a plurality of holes in a region of skin that includes one or more coring needles that can remove small cores of tissue by inserting and withdrawing the needles from the skin. A plurality of such needles can be affixed to a substrate to facilitate motion and positioning of all of the needles simultaneously. Insertion and withdrawal of the needles can be controlled by an actuator, which can control the positioning of the needles and/or the substrate, if present, via a mechanical coupling or actuation of an electrical or pneumatic translator or the like.

The exemplary system can further include a compression arrangement capable of or configured for applying a compression device or substance to deform the treated region after the holes are formed therein, For example, the compression arrangement can include a surgical stapler, a suturing device, an applicator capable of applying a stretched film or a curable/shrinkable liquid to the skin surface, etc.

The herein described exemplary embodiments pertain to cosmetic method and apparatus. It shall further be noted that the herein described cosmetic method has been tested, and is a safe and routine procedure that can be practiced in beauty parlors or other settings. The presented method is a minimally-invasive method, Moreover, the exemplary method is safe as it does not present a substantial health risk, and does not require professional medical expertise to be performed. No clinician is needed to perform the exemplary embodiments of the method described herein, and little or no risk, much less a health risk, is presented for a person being treated with said cosmetic method if standard cleanliness and sterilization procedures are employed, as shall become apparent from the following description.

Synergetic effects may arise from different combinations of the features and embodiments described herein, although all such combinations might not be described in detail Further, it shall be noted that all embodiments of the present disclosure concerning method or system according to the exemplary embodiment of the present disclosure, might be carried out with the order of the steps or procedures as described, nevertheless this has not to be the only and essential order of the steps of the procedures of the method and the system. All different orders and combinations of the steps and procedures are herewith described.

These and other objects, features and advantages of the present disclosure will become apparent upon reading the following detailed description of exemplary embodiments of the present disclosure, when taken in conjunction with the appended drawings and claims.

BRIEF DESCRIPTION OF THE DRAWINGS

Further objects, features and advantages of the present disclosure will become apparent from the following detailed description taken in conjunction with the accompanying figures showing illustrative embodiments, results and/or features of the present disclosure, in which:

FIG. 1 D is a top view of a lenticular-shaped hole that can be formed in skin tissue, in accordance with still further embodiments of the present disclosure;

Throughout the drawings, the same reference numerals and characters, unless otherwise stated, are used to denote like features, elements, components, or portions of the illustrated embodiments. Similar features may thus be described by the same reference numerals, which indicate to the skilled reader that exchanges of features between different embodiments can be done unless otherwise explicitly stated. Moreover, while the present disclosure will now be described in detail with reference to the figures, it is done so in connection with the illustrative embodiments and is not limited by the particular embodiments illustrated in the figures. It is intended that changes and modifications can be made to the described embodiments without departing from the true scope and spirit of the present disclosure as defined by the appended claims.

DETAILED DESCRIPTION OF EXEMPLARY EMBODIMENTS

Exemplary embodiments of the present disclosure relate to cosmetic methods and systems for generating a plurality of small holes in skin tissue and then manipulating or compressing the treated region in a particular direction, which can result in a locally directional reduction of skin surface area without visible scarring.

According to exemplary embodiments of the present disclosure, a plurality of small holes 100, such as the hole shown in the top view of FIG. 1A, can be formed mechanically in skin tissue, e.g., by a coring procedure as described in more detail below. The width or diameter of the holes 100 can be between 200 microns and 700 microns, or preferably between 200 microns and 500 microns. The small sizes of such holes can avoid the formation of visible markings or scars after the surrounding tissue heals. Forming holes in this size range is also well-tolerated and safe, because of the very small size of the damaged regions formed and the presence of undamaged adjacent tissue to promote rapid healing.

Figure 1A:
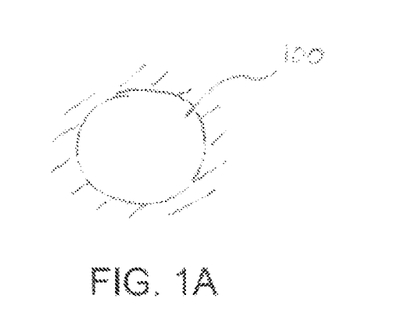
FIG. 1A is a top view of a round hole that can be formed in skin tissue, in accordance with exemplary embodiments of the present disclosure.
Figure 1B:
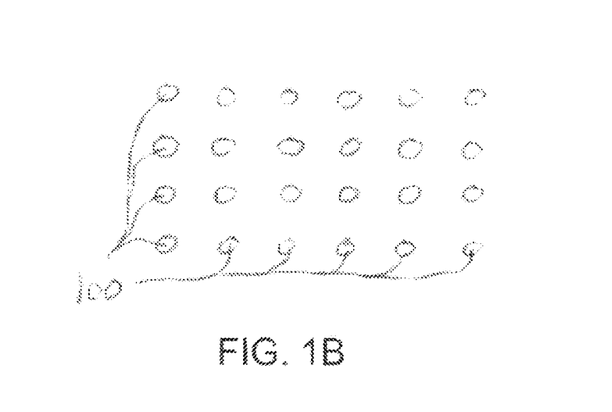
FIG. 1B is a top view of an array of the holes such as that shown in FIG. 1A.

The holes 100 can be substantially round as shown in FIG. 1A. A plurality of such holes 100 can be formed in a treatment region of skin or other tissue, e.g., as shown in FIG. 1B, to promote a general healing reaction over the treated region. Such a healing reaction may, for example, stimulate contraction of existing collagen and/or growth of new collagen in the treated region in response to the mechanical damage generated, by formation of the holes 100.

Figure 2:
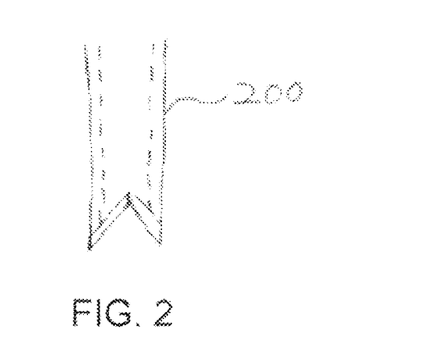
FIG. 2 is a schematic illustration of a coring needle that can be used to form small holes in a biological tissue such as skin, in accordance with exemplary embodiments of the present disclosure.

For example, the holes 100 can be formed using a pronged hollow needle 200 such as that shown in FIG. 2. This exemplary needle 200 has 2 pointed prongs, and can be formed, e.g., by abrading opposite sides of the distal end of a hollow needle at an angle relative to the axis of the needle. Other needle geometries can also be used, e.g., the needles 200 having more than 2 pointed prongs. Such pronged needle 200 (as opposed to, e.g., a. conventional biopsy-type needle having a circular cutting end) can facilitate penetration of the end of the needle 200 into the skin and removal of small cores of tissue to form the holes 100 without rotating the needle 200. These needles 200 can be formed, e.g., from conventional syringe needles having a gauge between about 19 and 27, e.g., having an internal diameter between about 700 microns (0.7 mm) and about 200 microns (0.2 mm). Preferably, the needle gauge can be between 21 and 27, corresponding to an internal diameter between about 0.5 mm and about 0.2 mm. Coring needles 200 can also be formed from other types of hollow tubes having an internal diameter corresponding to the desired bole width.

Insertion of the needle 200 into skin tissue, and subsequent withdrawal therefrom, can remove a core of tissue and form a microscopic hole 100. The needle 200 can be inserted to a depth that extends at least partially into the underlying dermal layer, or preferably through the entire dermal layer to the underlying subcutaneous tat layer. Inserting the needle 200 to at least the depth of the subcutaneous fat can facilitate removal of the tissue core within the needle lumen from the surrounding tissue, e.g., because the tissue core will be severed from the adjacent dermal tissue and the bottom of the tissue core is not strongly held by the underlying fat. Such mechanical coring procedures used to generate holes 100 may be accompanied by some minor bleeding, which is not significant and may tend to stop quickly because of the small hole sizes.

Figure 1C:
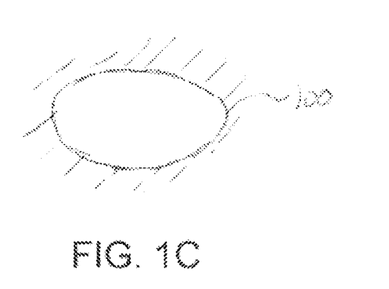
FIG. 1C is a top view of an elongated hole that can be formed in skin tissue, in accordance with further embodiments of the present disclosure.
Figure 1D:
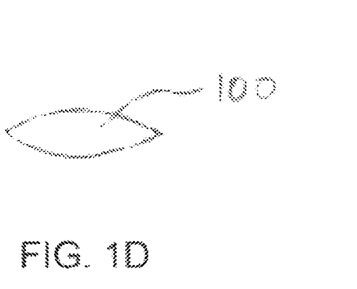

The hole 100 formed by a 2-pranged needle 200 may be somewhat elongated in shape, as shown in FIG. 1C. This non-circular shape can result from the slightly asymmetrical tissue stretching and cutting that can occur when the 2 prongs of the needle 200 pierce the tissue and advance within it. For example, the hole 100 formed using a 2-pronged coring needle 200 can have an aspect ratio (e.g., ratio of length to width in cross-section) of about 3:2 at or near the tissue surface.

Other hole shapes can be formed in accordance with certain exemplary embodiments of the present disclosure, such as the lenticular-shaped hole 100 shown in FIG. 1 D. For example, the aspect ratio of the lenticular hole 100 in FIG. 1 D can be, e.g., about 3:1, and the angle at which the curved sides meet can be about 30 degrees. This ratio (or an aspect ratio close to this) and geometry can facilitate closure of the hole 100 by reducing associated stresses or deformations in the surrounding tissue. Although the shape of an actual lenticular hole 100 formed in soft tissue may not have precisely smooth edges and sharp corners as illustrated in FIG. 1D an approximately lenticular shape may facilitate closure of such holes 100 as they heal.

In general, the specific shape(s) of the holes 100 may not be important and/or critical because the small size scale facilitates approximation of the bole edges in any desired direction without generating unwanted effects such as "dog ears" or misalignments when they close and heal together. Needles 200 having more prongs, e.g., 3 or 4 prongs, can be used in further embodiments, where such needles 200 may tend to produce rounder holes 100 such as those shown in FIG. 1A.

In further exemplary embodiments of the disclosure, formation of microscopic holes 100 in tissue that are asymmetric or noncircular, such as the hole 100 shown in FIG. 1C, can be desirable for generating closure of holes 100 that is locally and/or macroscopically directional Such holes 100 that are asymmetric may be closed more easily, e.g., by compressing die tissue such that the narrow width is further narrowed and opposite sides of the hole 100 are brought into proximity or contacted with each other. Asymmetric holes 100 can be formed using a variety of techniques and apparatuses in accordance with embodiments of the present disclosure.

In one exemplary embodiment, elongated holes 100 can be formed in tissue by stretching the tissue in a direction, and then forming the holes 100 in the tissue, e.g., using a mechanical coring needle 200, or another mechanical device. Upon allowing the tissue to relax, the hole 100 will tend to be somewhat elongated, such as the hole 100 shown in FIG. 1 C.

In further exemplary embodiments, the coring needle 200 can be provided in various shapes, e.g., having an elongated non-circular cross section, such that the holes 100 formed in the skin or other tissue by inserting and withdrawing the needle 200 will be elongated in shape.

In general, the shape of a microscopic hole 100 formed in soft skin tissue may not have precisely smooth edges and a well-defined shape, and the precise shape of the holes 300 may not significantly affect the subsequent directional shrinkage or closure behavior because of their small size (e.g., 0.7 mm or less).

The holes 100 can be formed mechanically such that the fraction of surface area removed in the treated region is between about 5% and 50%, e.g., between about 10% and 30%. Such area fractions of removed tissue can be small enough, to promote healing or recovery of the mechanically damaged skin by retaining a sufficient amount of healthy tissue around each hole 100, while being large enough to generate a cosmetically desirable amount of shrinkage in a single exemplary procedure performed on the treated region as described, herein. The particular area fraction of holes 100 can be selected based on factors such as, e.g., the desired extent of shrinkage, the location of the treated region (e.g., face, neck, arms, etc.), general skin characteristics, etc.

The distribution of the holes 100 can be substantially random, or formed in any of various patterns. For example, a plurality of holes 100 can be formed in the skin or other tissue in a generally square or rectangular array. In further embodiments, the holes 100 can be formed in an array of staggered rows, or in a random pattern. The particular arrangement or pattern of the holes 100 may not be particularly important with respect to shrinkage behavior, e.g., because of the large number and small size of the holes 100 in the treated region.

A pattern of the holes 100, such as that shown in, e.g., FIG. 1B, can be formed using a variety of techniques. For example, the holes 100 can be formed mechanically; e.g., using a reciprocating mechanism that traverses the tissue to form the pattern. The mechanism can include one or more rows of the coring needles 200, such that staggered rows of the holes 100 can be generated in the skin tissue. In further exemplary embodiments, the holes 100 can be formed in other patterns that may not be rows, e.g., in spatially random arrangements, which can be achieved by repeated manual insertion and withdrawal of one or more needles 200 at various locations in the treated region.

The density or proximity of the holes 100 can also be varied in different regions of the tissue being treated. For example, the holes can be spaced further apart in the peripheral areas or edges of a particular treated region. Such, "feathering" of the removed tissue volume can facilitate a smoother or gradual transition between the shrunken or tightened skin within the treatment region and the untreated region of tissue surrounding it. However, such "feathering" or density gradients of the holes 100 may not be particularly important for obtaining a continuous directional shrinkage over the treated region, because the large number of small holes 100 can adjust to gradients in skin deformation during the subsequent healing process. For example, the large number and moderate to high density of microscopic holes 100 can accommodate macroscopic gradients m shrinkage with only very minor local differences in the closure and healing behavior of each, individual hole 100. Such gradients and directionality can: be produced, e.g., by the exemplary manipulation of the treated region after the holes 100 are formed, as described herein below.

The particular shape and size of the treated region in which the holes 100 are formed is arbitrary; and can be selected based on the areas of skin that may benefit from the exemplary methods described herein. Such methods can be effective over both small regions (e.g. on the order of a square cm or less) and larger regions, because of the large number of sub-millimeter holes 100 used to achieve cosmetic effects as described, herein. For example, the small size of the holes 100 generated at an areal fraction between about 5% and 50% can provide a substantially uniform dispersion of such holes 100 when viewed at size scales of about 1 cm or larger. Accordingly, the exemplary methods described herein can. include directional closure of a large number of small holes 100, which can well accommodate any gradients in shrinkage that may result within or adjacent to a particular treatment region, and which may be applied in treatment regions having arbitrary shapes and extents.

After the holes 100 are formed in skin or other tissue, as described above, it is possible to promote closure of the holes 100 by applying appropriate lateral forces (e.g., compressive or tensile forces) to the tissue in the treated region as it heals. Such forces can facilitate contact between opposite edges of the holes 100, particularly near the tissue surface, and increase overall shrinkage of the tissue as the holes 100 heal in a closed configuration. Further, anisotropy or directionality of the overall skin shrinkage in the treated region following formation of the holes 100 can be achieved by application of such forces in a particular direction during the subsequent healing or recovery processes.

Figure 3A:
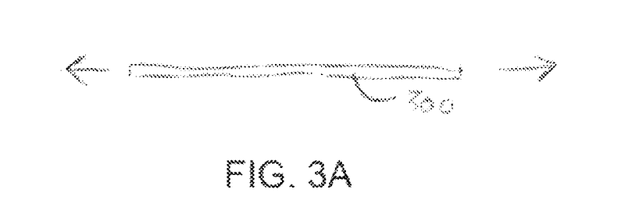
FIG. 3A is a schematic side view of a stretch film, in accordance with further exemplary embodiments of the present disclosure.
Figure 3B:
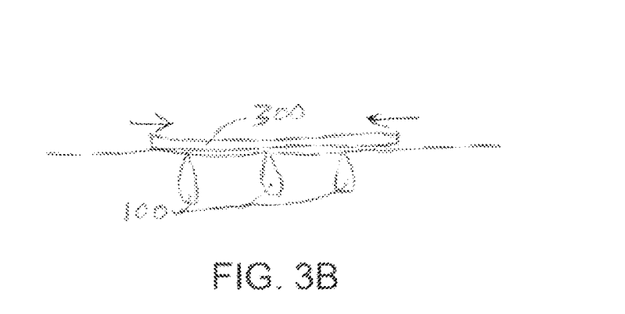
FIG. 3B is a schematic side view of the exemplary film shown in FIG. 3A being applied to the surface of a region of skin containing holes therein.
Figure 3C:
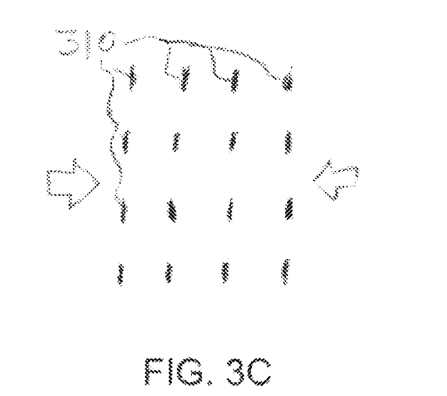
FIG. 3C is a schematic top view of the region of skin shown in FIG. 2B with the exemplary film applied to the surface thereof.

In one exemplary embodiment of the present disclosure, a stretch film 300 can be used to provide a compressive surface force to the tissue surface in the treated region and promote hole closure. For example, as shown in FIG. 3A, the film 300 can be pre-stretched in the direction of the arrows. The stretch film 300 can then be adhered to the tissue surface, as shown in the exemplary cross-sectional view of the treated region in FIG. 3B. The pre-stretched film 300 can then generate a directional compressive force along the tissue surface, as shown by the arrows in FIG. 3B. This force can pull together the edges of the holes 100, particularly near the tissue surface, to facilitate hole closure and increased shrinkage of the tissue during the healing process. For example, the stretch film 300 can be applied such that the direction, of compressive forces at the tissue surface (indicated by the arrows In FIG. 3B) is in the preferred direction of shrinkage. Hole closure resulting from such compressive forces can result in a closed-hole configuration similar to the exemplary configuration shown in the top view of the treated region of FIG. 3C, where the arrows represent the direction of compressive forces, and the small vertical lines 310 represent the approximated, edges of the holes 100 at the skin surface.

Materials that can be used to form the film 300 include Tegaderm™, another stretchable polymer, or the like. For example, Tegaderm™ has adherent properties and can be stretched up to about 30-40% and then applied to the tissue surface. Other film materials can also be used in further embodiments. Such films can be provided with an adhesive surface, or alternatively can be adhered to the tissue surface using any appropriate biocompatible glue, cement, or adhesive.

For example, the compressive film 300 can be maintained on the tissue, surface for several days, e.g. about 4-6 days, to facilitate sufficient healing or modification of the skin tissue while it is held in a compressed state, e.g., to minimize or prevent re-opening of the holes 100 or collagen expansion in the compressive direction by external forces.

Figure 3D:
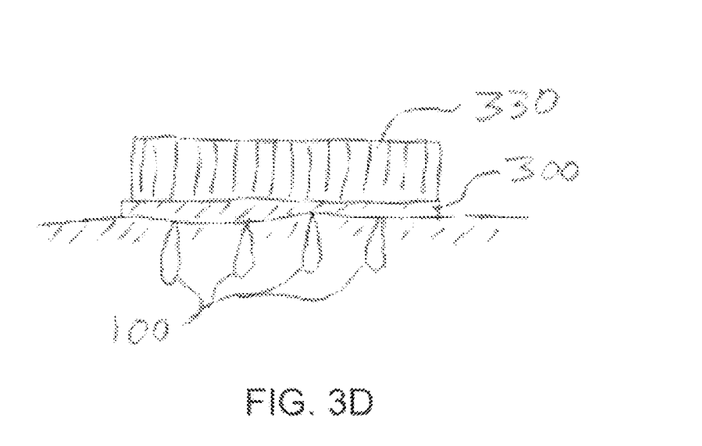
FIG. 3D is a side view of the exemplary film applied to the surface of the region of skin as shown in FIG. 3B, with a rigid object adhered to the top of the stretch film to stabilize it mechanically.

In further exemplary embodiments, a stabilizing film 330 (shown in FIG. 3D), e.g., a non-stretching film or rigid plate or the like, can be adhered to the upper surface of the film 300 after it has relaxed and compressed the tissue surface. This stabilizing film 330 can provide mechanical stability to the compressed tissue surface to maintain the compressive state and constrain further displacement, (e.g., relaxation) of the compressed tissue during the healing process, for example, to prevent relaxation of the film 300 during the recovery process or prevent detachment of the film 300 from, the skin surface. In certain exemplary embodiments, the stabilizing film can be adhered directly to the skin surface surrounding the treated region, e.g., beyond the edges of the stretch film 300, instead of or in addition to being adhered to the top of the stretch film 300.

Figure 4A:
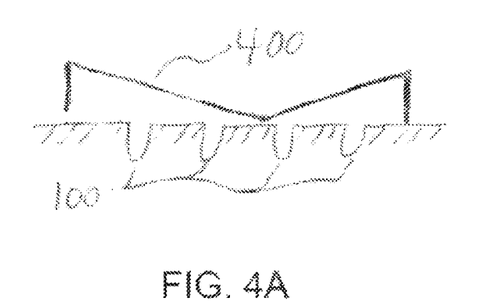
FIG. 4A is a schematic side view of a surgical staple that can be used to compress a region of skin tissue, in accordance with further exemplary embodiments of the present disclosure.
Figure 4B:
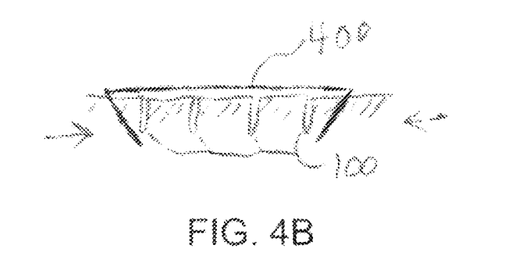
FIG. 4B is a schematic side view of the staple shown in FIG. 4A that is applied to a region of skin containing holes therein.

In another exemplary embodiment of the disclosure, one or more surgical staples 400 can be used to apply and maintain a compressive force on the treated region, as shown in the exemplary cross-sectional views of a treated region in FIGS. 4A and 4B. An exemplary large surgical staple 400 (e.g., a staple large enough to span across a plurality of holes 100) is positioned over the treated region in FIG. 4A, FIG. 4B shows the compressive deformation of the treated region by the inserted staple 400. The exemplary staple 400 can be used to provide a general compression of the treated region of skin, thereby approximating the edges of a plurality of holes 100, as shown in FIG. 4B, rather than approximating two opposing edges of a single incision or wound (as is typically done with conventional applications of surgical staples). Such exemplary use of one or more surgical staples 400 may provide increased compression of the skin below the surface of the treated region as compared to that provided by application of a stretch film 300 to the skin surface (shown in FIG. 3B), because of the anchoring and pulling together of tissue, below the surface by the staple 400.

Figure 4C:
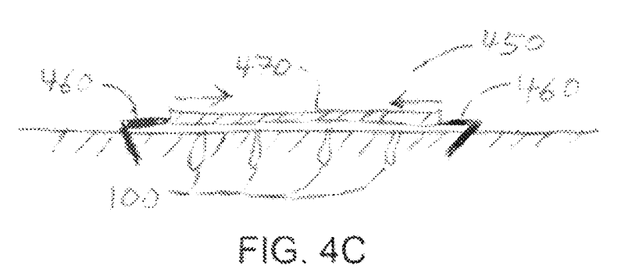
FIG. 4C is a schematic side view of a tensioning clip that is applied to a region of skin containing holes therein in accordance with certain exemplary embodiments of the disclosure.

In another exemplary embodiment, a tensioning clip 450 as shown in FIG. 4C can be used to apply and maintain a compressive stress in the treatment region. The clip 450 includes two prong arrangements 460 capable of being inserted into skin. The prong arrangements 460 can have a sharp point or edge at their distal ends to facilitate penetration into the skin, and can be made from any material sufficiently rigid or strong to support a stress as described below without breaking or deforming significantly (e.g., a metal or rigid plastic or the like). The prong arrangements 460 can be connected, by an elastic material 470, which can be provided as a strap, cord, or the like (e.g., similar to a rubber band, small bungee cord, or the like). The elastic material 470 can be stretched and the prong arrangements 460 then inserted into skin within and/or adjacent to the treatment region that contains holes formed as described herein. The stretched elastic material 470 can then cause the prong arrangements 460 to exert a compressive force between them, as shown by the arrows in FIG. 4C. In this manner, a compressive stress can be generated and maintained over at least a portion of the treatment area using a tensioning clip 450 that can be easily inserted into and removed from the skin. The size of the prong arrangements 460 and elastic material 470 can be selected based on the size of the treatment region and/or portion of such region over which a stress is to be maintained.

According to certain exemplary embodiments, a plurality of staples 400 and/or tensioning clips 450 can be applied within and/or across an entire treated region, or a portion thereof. In further embodiments, staples 400 and/or tensioning clips 450 can be oriented in different directions on or across the treated region to vary the local preferred direction of shrinkage and/or to provide increased non-directional shrinkage of the treated region (e.g., as compared to a conventional fractional damage procedure that does not compress the treated region after holes 100 are formed).

The staple(s) 400 and/or tensioning clips 450, if used, can be retained in the treatment region for several days, e.g. about 4-6 days, to maintain a compressive state therein dining the healing/recovery process, thereby allowing sufficient healing or modification of the skin tissue while it is held in a compressed state. Further, the staples 400 and/or tensioning clips 450 can be small or thin in at least one direction, to avoid formation of visible markings upon their removal. In certain exemplary embodiments, staples 400 and/or tensioning clips 450 can be used that are thin and/or that include several prongs configured to pierce the skin. Such staples 400 and/or tensioning clips 450 can provide compressive forces comparable to a single large staple 400 or clip 450 while allowing the individual prongs to be smaller in size to reduce or eliminate formation of markings when such staples 400 and/or tensioning clips 450 are removed.

Figure 5A:
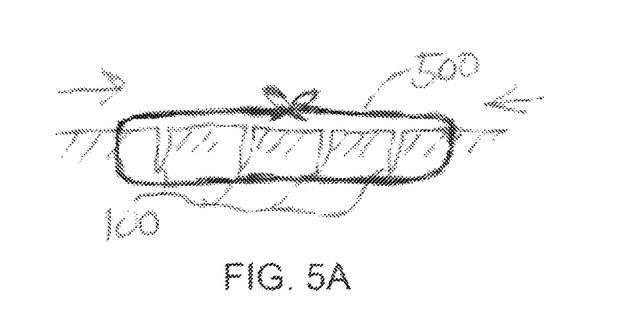
FIG. 5A is a schematic side view of a suture that can be used to compress a region of skin tissue, in accordance with further exemplary embodiments of the present disclosure.

In yet another exemplary embodiment of the disclosure, one or more sutures 500 can be applied to the treated region, apply to maintain a compressive force thereon, as shown in the exemplary cross-sectional view of FIG. 5A. Each suture 500 can be large enough to span across a plurality of holes 100, thereby promoting directional approximation of opposing surfaces of the holes 100, as shown in FIG. 5A. Similar to the staple 400 shown in FIG. 4B, the suture 500 may provide increased compression of the skin below the surface of the treated region as compared to that provided by application of a stretch film 300 to the skin surface.

Figure 5B:
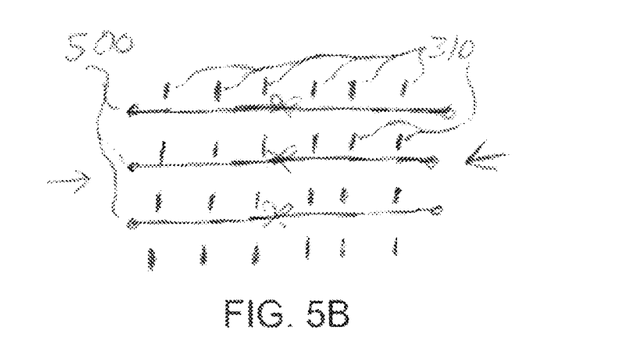
FIG. 5B is a schematic top view of a plurality of sutures such as that shown in FIG. 5A that are applied to a region of skin containing holes therein in a first configuration.
Figure 5C:
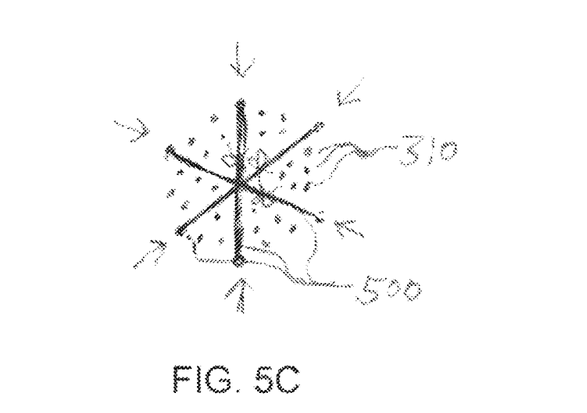
FIG. 5C is a schematic top view of a plurality of sutures such as that shown in FIG. 5A that are applied to a region of skin containing holes therein in a second configuration.

According to certain exemplary embodiments, a plurality of sutures 500 can be applied within and/or across an entire treated region, or a portion thereof. For example, a plurality of the sutures 500 can be applied substantially parallel across the treated region, as shown in the exemplary top view of FIG. 5B. The arrows in FIG. 5B indicate the direction of compressive forces, and the small vertical lines 330 represent the approximated edges of the holes 100 at the skin surface, in another exemplary embodiment, the sutures 500 can be applied in different directions over the treated region, such as in the exemplary configuration shown in the top view of FIG. 5C to provide increased non-directional shrinkage of the treated region. The arrows in FIG. 5C represent the local direction of compressive forces, which may tend to omni-directionally or isotropically compress the edges of the holes 100 at the skin surface. In still another exemplary embodiment, the sutures 500 can be oriented in different directions within or across the treated region to vary the local preferred direction of shrinkage within the treated region.

Similar to the stretch film 300 and the staple 400, the suture(s) 500, if used, can be retained in the treatment region for several, days, e.g. about 4-6 days, to maintain a compressive state therein during the healing/recovery process, thereby allowing sufficient healing or modification of the skin tissue while it is held in a compressed state.

According to further exemplary embodiments, other devices and techniques can also be used to apply and maintain compressive forces to the perforated tissue in the treated region, such as, e.g., forceps, adhesive heat-shrink films, surface application of curable liquids such as polymer precursors that can shrink and adhere to the skin surface as they cure, etc. Any-such heat-shrink films, curable shrinking liquids, and the like that are known in the art may be used with certain embodiments of the present disclosure.

In still further exemplary embodiments, any combination of stretch film 300, staples 400, sutures 500, heat-shrink films, and/or curable liquids can be used to apply and/or maintain stresses or deformations in the treated region as the holes 100 heal.

According to yet further exemplary embodiments, a tensile force can be applied to a surface region of tissue to promote closure of holes 100 formed therein. For example, a plurality of holes 100 can be formed in a tissue as described herein and shown in FIG. 6A. A tensile force can be applied to the tissue m the direction of the arrows shown in FIG. 6A. Such exemplary tensile force can locally stretch the tissue in the direction of the arrows, which may cause the lateral sides of the holes to approach and/or contact each other as shown in FIG. 6B. Such narrowing of the holes 100 can facilitate closure and healing, and result in local directional shrinkage of the tissue in a direction orthogonal to the applied tensile force as the holes heal, while tending to maintain or even slightly expand the skin in the direction of the tensile forces as the tissue damage caused by formation of the holes 100 heals.

Figure 6A:
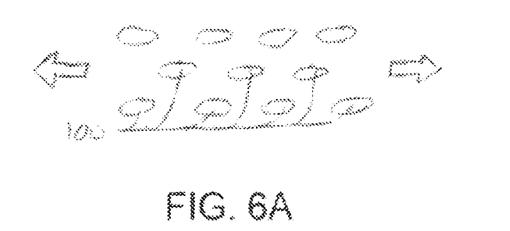
FIG. 6A is a schematic top view of a tensile stress being applied to a region of skin containing holes therein.
Figure 6B:
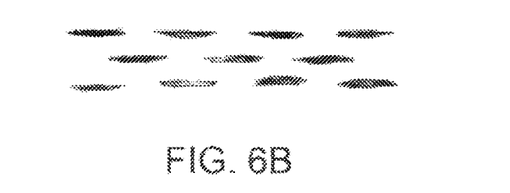
FIG. 6B is a schematic top view illustrating the effect of the tensile stress shown in FIG. 6A on the holes.

The tensile force, as illustrated in FIG. 6A, can be applied using any of a variety of techniques and/or devices. For example, such force can be applied manually, e.g., by pressing fingers against the skin at opposite sides of the treated region, adjacent to the perimeter thereof. The fingers can then be spread apart to apply the tensile force to the tissue, e.g., to stretch the region of tissue between the finger contact points. A rigid or non-stretchable adhesive film or plate can then be adhered to the stretched tissue to inhibit or prevent relaxation of the tissue—as the holes heal thereby maintaining the tissue in a stretched or tensile state. In a further embodiment, an expander device can be used that includes two or more contact surfaces that can be spread apart, e.g., a pair of forceps or the like having a flat contact area on the end of each tip. In a similar manner, the contact areas can be pressed against the tissue and then moved apart mechanically to stretch the tissue between the contact areas. The contact areas can be provided with a rough, non-slip, and/or adhesive surface to maintain contact with particular locations on the skin or tissue surface as the tensile force is applied, and the expander device can be configured to maintain the expanded configuration while it is adhered to the skin surface. Other techniques to stretch the skin locally may also be used with embodiments of the present disclosure.

Various additional procedures can be used to promote hole closure and healing of the holes 100 after they are formed in the tissue. For example, the holes 100 can be exposed to saline or other solutions after they are formed, to promote hydration and softening of the tissue prior to healing. Such solutions can also facilitate removal of debris or impurities in the holes, e.g., removal of blood that may be present after the holes 100 are formed mechanically using one or more of the coring needles 200.

In further exemplary embodiments, biocompatible glues or adhesives can be used to facilitate more rapid adherence of the closed holes 100, e.g., during the healing process. For example, photochemical tissue bonding (PTB) techniques can be used to help attach the holes 100 in a closed configuration during the healing process. In a PTB process, a photosensitizer (e.g., rose bengal, riboflavin, porphyrins, chlorins, and the like) can be applied, to the tissue after the holes 100 have been formed therein, but prior to applying the compressive film. 300 or a compressive or tensile force as described herein. Photosensitizer precursors including, e.g., pro-drugs of such photosensitizers, can also be used, where such precursors may be metabolized or otherwise activated to form, photosensitizers in the tissue. Such photoactive substances (e.g., photosensitizers or precursors) can promote tissue bonding when applied to tissue, optionally activated or allowed to metabolized, and then exposed to light having one or more appropriate wavelengths.

After the holes 100 are directionally compressed using the stretch film 300, staple(s) 400, suture(s) 500, and/or other compressive or tensile forces, the tissue can be exposed to light having an appropriate wavelength to activate the tissue bonding, to promote adhesion of the hole walls within a few minutes. The choice of wavelength can be based on the particular photosensitizer or precursor used. The material and/or object(s) imposing compressive and/or tensile forces in the treated region can then be removed while the holes 100 remain closed at the tissue surface and continue to heal.

According to yet further exemplary embodiments, the stretch film 300 can be provided with a layer of one or more photosensitizers or precursors, such that at least a portion of the photoactive substance(s) is transferred onto the tissue surface when the film 300 is applied to the surface of the tissue. For example, the photoactive substance(s) can be provided in a gel or micro-encapsulated layer on the surface of the film 300 that is placed against a skin surface. The activating light can then be directed through the top surface of the film 300 and onto the compressed tissue surface and the photoactive substance applied thereon, in general one or more of the various conventional photochemical tissue bonding systems, materials, and methods can be used to facilitate more rapid hole closure in accordance with embodiments of the present disclosure.

In further exemplary embodiments, other tissue glues such as, e.g., cyanoacrylates, can be used to glue the holes 100 together after they are formed and compressed, stretched and/or closed. It may be preferable to limit application of such glue to the tissue surface and avoid introduction of them within the holes 100, to avoid filling them with unwanted material that may inhibit subsequent hole closure and shrinkage. The use of any conventional tissue-bonding techniques or tissue glues, including those described herein, can reduce the amount of time that the compressive film 300 or other dressings are maintained over the treated tissue area as it heals, while preventing re-opening of the closed holes 100 during the gradual healing process.

As described herein, the shape, density or spacing, and pattern or spatial distribution of the holes 100, and/or the orientation of an applied compressive or tensile force to the surface of the treated region, can provide a directionally-oriented shrinkage of the tissue as it heals. Such directionality can be utilized to achieve improved cosmetic results by generating increased shrinkage in a preferred local direction in a mechanical fractional resurfacing procedure, A plurality of such procedures can be applied to a particular treated region to obtain greater overall shrinkage of the skin or other tissue, preferably allowing sufficient healing time between subsequent treatments on a particular area. The compressive and/or tensile directions can be varied in different treatments of a single area to obtain a more homogenous shrinkage of tissue in the area. The sizes and preferred shrinkage directions of adjacent treated regions can also be selected and varied to achieve desirable overall shrinkage patterns for the skin or other tissue.

Application of a tensile or compressive force to the tissue to promote hole closure can also affect the characteristics of collagen that may be formed during the hole closure and tissue healing processes that occur after the holes 100 have been formed. For example, collagen may grow and/or align in particular directions when forming in tissue that is deformed by application of external forces after the formation of the holes 100, as described herein. Such modification of collagen growth and/or alignment in the treated tissue may provide further desirable cosmetic effects.

Figure 7:
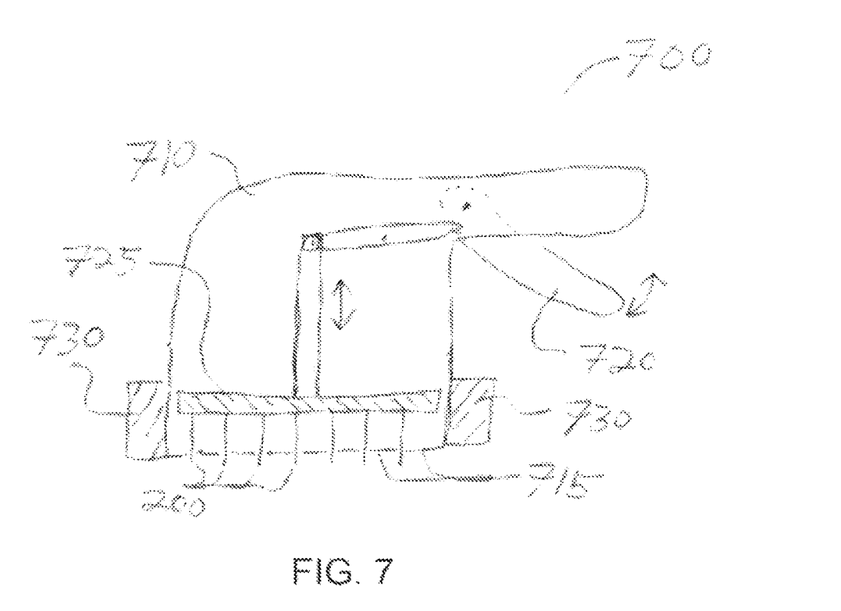
FIG. 7 is a schematic side view of an exemplary apparatus for mechanically generating fractional damage in tissue and providing a compressive stress to the tissue, in accordance with further exemplary embodiments of the present disclosure.

In further exemplary embodiments of the present disclosure, a system can be provided to generate a plurality of the holes 100 in a treated region of skin, and then apply a compressive or tensile force to the treated region. For example, an exemplary system 700 can be provided that includes a handpiece 710 having a lower surface 715, a plurality of retractable coring needles 200, an actuator handle 720, and a compression arrangement 730, as shown in FIG. 7. The needles 200 can, e.g., be affixed to a movable substrate 725 as a needle array or the like to facilitate their controllable motion and positioning relative to the Sower surface 715. According to certain exemplary embodiments, the needles 200 and the substrate 725 can be provided together as a single unit or cartridge, which can be disposable or reusable/sterilizable. The lower surface 715 can be configured and/or structured to be placed on the surface of a treated region, and the actuator handle 720 can be capable of positioning and/or maintaining the needles 200 and/or the substrate 725 at one or more locations relative to the lower surface 715.

A number of the needles 200 and area of the needle array can be selected based on various factors. For example, a number of the needles 200 can be large enough to facilitate rapid treatment of large areas of skin, but not so large that the cost and complexity of the needle array becomes prohibitive. Further, it may be difficult to insert a large number of the needles 200 into the skin simultaneously. For example, such number of the needles 200 can be between, e.g., 1 and 50, or between about 6 and 25. In certain exemplary embodiments, a larger number of the needles 200 can be provided in the system 700. The average spacing between the needles 200 can be selected based on the timer diameter of the needles 200 and the desired fractional area of skin to be removed by a single insertion and withdrawal of the needles 200, using simple geometric calculations.

In an exemplary configuration, the system 700 can (e.g., initially) be configured such that the distal ends of the needles 200 protrude a particular distance below the lower surface 715. Such exemplary distance can be, e.g., the approximate depth of the local dermis of the treated region. In certain embodiments, such distance can be adjustable (for example, using a threaded adjuster or stop, a plurality of stepped settings or the like, not shown) such that the system 700 can be used to treat skin having various thicknesses.

The exemplary system 700 can be applied onto a treated region until the lower surface 715 of the system 700 contacts the skin surface, such that the needles 200 penetrate the skin tissue to the particular distance into the skin, e.g., through the entire thickness of the dermis. The actuator handle 720 can then be squeezed to retract the needles from the skin, pulling the distal ends of the needles 200 above the lower surface 715 and forming a plurality of holes 100 in the skin. The actuator handle 720 can be further capable of activating the compression arrangement 730 (not shown) to apply a compression element to the treated region after the needles 200 have been withdrawn from the treated region.

In one exemplary embodiment, the compression arrangement 730 can include a surgical stapler configured to be mechanically or electrically actuated by the actuator handle 720, such that squeezing the actuator handle 720 will first withdraw the needles 200 from the treatment site and then apply one or more large staples 400 and/or tensioning clips 450 across at least a portion of the treated region as described herein above.

According to another exemplary embodiment, the compression arrangement 730 can include a suture needle (e.g. a curved needle) and suture thread. The compression arrangement 730 can be capable of or configured for introducing one or more lengths of suture thread below the surface of the treated region, e.g., with the ends of the thread protruding from the surface of the skin, when it is actuated by the actuator handle 720, after the needles 200 are withdrawn from the treatment site. The ends of the suture thread can then be tied together to form a suture 500 that can apply a compressive force to the skin tissue in the treated region as described herein above. Optionally, the compression arrangement 730 can be capable of or configured for tying off the suture thread when actuated, e.g., at a preselected tension.

In yet another exemplary embodiment the compression arrangement 730 can include a stretch film applicator that is capable of and/or configured for adhering a stretch film 300 or the like over the treated region after the needles 200 are withdrawn from the skin. For example, the compression arrangement 730 can include a small roll of stretch film 300 configured similar to a packing tape dispenser. The system 700 can be translated over the treated region after the needles 200 are withdrawn, to apply the film 300 over the holes 100 just formed. The film 300 can also be provided in pre-cut pieces that, are sized to fit over the treated region.

According to a further exemplary embodiment, the compression arrangement 730 can include a reservoir of a curable coating material, as described herein above, and it can be capable of applying such coating material to the surface of the treated region after the needles 200 are withdrawn from the skin. In another embodiment, the compression arrangement 730 can be configured or adapted to apply a photoactivated material (or precursor of such material), as described herein above, to at least a portion of the treated region, and directing light energy onto the region to activate the material Embodiments of the system 700 in which the compression arrangement 730 is capable of applying other types of compression or tensioning elements to the treated region after the holes 100 are formed also MS within the scope of the present disclosure.

EXAMPLE

An exemplary procedure in accordance with certain exemplary embodiments of the present disclosure was performed on the lower abdomen of a swine animal model to demonstrate the ability to produce directional shrinkage. Six test sites, each approximately a 3 cm by 3 cm square, were tattooed onto the animal at Day 0. Seven control sites of the same size were also marked between the test sites. The control sites were included to account for net growth of the animal over the course of observations.

For example, 144 uniformly-distributed holes were made through the depth of the skin in each test site using a specially designed vacuum-assisted 19 gauge coring needle. The holes were formed in a substantially random array by manually inserting and withdrawing the coring needle 144 times at arbitrary locations within the test sites. The width of the holes formed was approximately the same as the inside diameter of the needle, e.g., about 0.69 mm. This corresponds to a fractional surface area removal within each test site of about 6%. This corresponds to a relatively low fractional amount of skin tissue removed within the preferred ranges described herein.

A pre-stretched sticky dressing (Tegaderm™) was then adhered onto the test sites and allowed to retract towards its original size, thus compressing the tissue as described herein above. Test sites 1, 2, 4, 5 and 6 were compressed along the langer lines that run approximately horizontally from head to tail (e.g., in the X direction). Test site 3 was compressed across the langer lines (in the vertical or Y direction). No stretched film was applied to the seven control sites.

The dressing was left in place on each test site for seven days and then removed. The animal was observed, photographed and the width and height of each test and control site were measured until day 28.

Figure 8A:
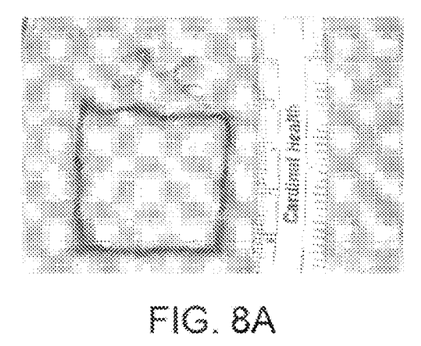
FIGS. 8A-8C are exemplary images of a region of porcine skin taken at various times, showing the size and shape changes arising from fractional damage generated therein followed by applied stresses.
Figure 8B:
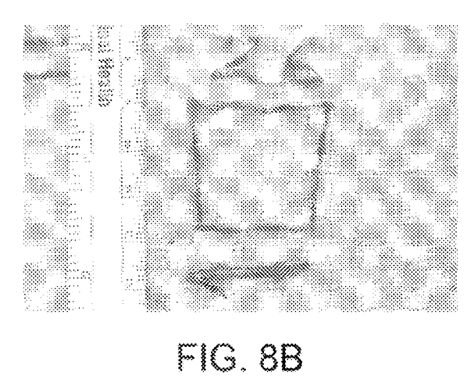
Figure 8C:
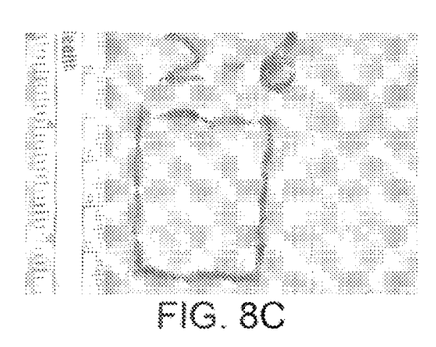

Photographic images of test site 6 taken at Day 0 (pre-treatment). Day 7 (when the dressing was removed), and Day 28, are shown in FIGS. 8A, 8B and 8C, respectively. The sizes of these images were adjusted such that the ruler length is the same in each. The overall shape of the test site changed from substantially square to rectangular from Day 0 to Day 28, with the width of the test site (in the direction of compression, along the langer lines being about 12% smaller at the end of observation compared to the initial size of the test site. The height of the test site (orthogonal to the compression direction) increased by about 17% by Day 28 as compared to the pre-treatment height on Day 0. Further, no apparent scarring or markings are evident in these images, consistent with the expected cosmetic advantages of reducing skin area by formation of many very small holes.

Table 1 below shows the measured width and height (X and Y, respectively) of each test site on Day 0, Day 7, and Day 28. The data suggest that the width of sites 1, 2, 4, 5 and 6 decreased slightly over the course of the observations-, and that they tended to widen a bit between Day 7 (when the compressive dressing was removed) and Day 28, which may be partially attributed to relaxation of the unconstrained skin. The width of test site 3 increased between Day 0 and Day 7 because this site was compressed in the vertical direction, orthogonal to the other test sites. Similarly, the height of the test sites (except for site 3), orthogonal to the compressive direction, appears to have remained about the same or increased slightly between Day 0 and Day 20.

TABLE 1

Measured dimensions of each test site (in cm) at Day 0, 7, and 28

| Test Site | Day 0 X | Day 0 Y | Day 7 X | Day 7 Y | Day 28 X | Day 28 Y |
|---|---|---|---|---|---|---|
| 1 | 3.4 | 3.1 | 2.8 | 2.8 | 3.2 | 3.4 |
| 2 | 3.2 | 3.0 | 3.0 | 2.8 | 3.25 | 3.3 |
| 3 | 3.15 | 3.0 | 3.8 | 2.3 | 3.1 | 2.95 |
| 4 | 3.8 | 3.0 | 3.3 | 2.7 | 3.4 | 3.1 |
| 5 | 3.2 | 3.2 | 3.2 | 3.05 | 3.05 | 3.2 |
| 6 | 3.4 | 2.9 | 2.7 | 2.6 | 3.0 | 3.4 |

It should be noted that there was some net growth of the animal, subject over the course of the observations. To correct for this, the width and height of each control site was measured at Day 0, 7 and 28. The measured width and height of each test site was then normalized by the average width and height, respectively, of the control sites measured on the same day. This provides a rough correction for overall growth of the animal subject (i.e., general, increase in skin area) between measurements of the test site dimensions. Table 2 below includes the width and height of each control site as measured on Day 0, 7, and 28.

TABLE 2

Measured dimensions of each control site (in cm) at Day 0, 7, and 28

| Control Site | Day 0 X | Day 0 Y | Day 7 X | Day 7 Y | Day 28 X | Day 28 Y |
|---|---|---|---|---|---|---|
| b | 3.0 | 2.6 | 3.3 | 2.5 | 3.95 | 3.4 |
| c | 3.15 | 2.7 | 3.25 | 2.0 | 3.9 | 3.15 |
| d | 2.9 | 2.6 | 2.95 | 1.8 | 3.5 | 3.2 |
| e | 2.95 | 2.55 | 2.9 | 2.6 | 3.45 | 3.4 |
| f | 3.0 | 2.4 | 3.0 | 2.4 | 3.6 | 3.1 |
| g | 3.1 | 2.5 | 3.15 | 2.15 | 3.5 | 3.15 |
| h | 2.9 | 2.6 | 2.8 | 2.7 | 3.65 | 2.9 |
| Average | 3.0 | 2.56 | 3.05 | 2.31 | 3.65 | 3.18 |

Figure 9A:
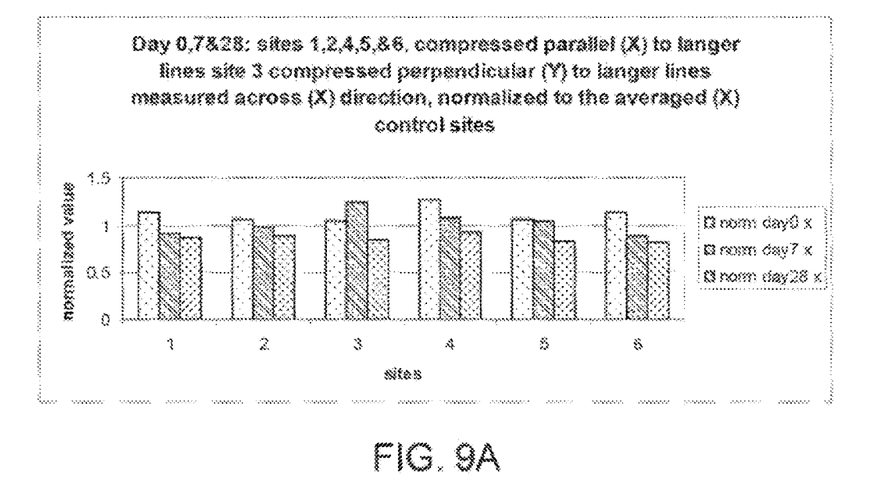
FIGS. 9A and 9B are bar graphs of exemplary data showing the observed changes in width and height of regions of porcine skin fractionally damaged with coring needles, normalized by corresponding size changes of untreated regions.
Figure 9B:
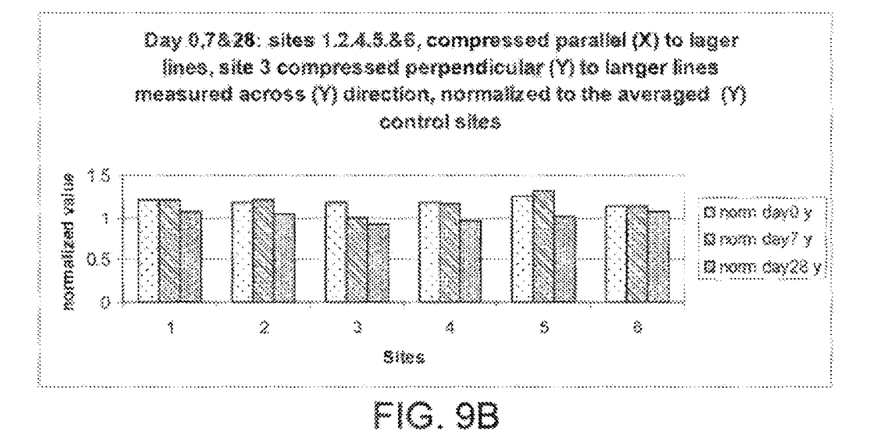

Bar graphs showing the normalized width and height (X and Y, respectively) of each test site are shown in FIGS. 9A and 9B, respectively. The data in these graphs suggest that there was a noticeable decrease in width of test sites 1, 2, 4, 5 and 6 over the 4 weeks following the initial, treatment, when overall growth of the animal subject was accounted for. There also appears to also be a slightly less-marked decrease in the height of these test sites (orthogonal to the compressive direction) over the same period. Thus, there appears to be some preferred directionality in the shrinkage of the test subject skin when treated in accordance with embodiments of the present disclosure.

The observed effects (and differences in behavior between the X and Y directions) are somewhat modest in this exemplary study. A few factors should be noted when assessing these measured results, First, there are qualitative differences between human and swine skin. It is expected that human skin, being thinner and less resilient, may be more affected under similar treatment conditions. Second, the fractional area of skin removed in each test area was only 6%, which is relatively low. More marked results are likely to appear if a larger number of holes was formed within each test area (corresponding to a larger fraction of skin-removed, e.g., up to 25-30% or more). Also, the dressing did not always adhere very well to the skin of the animal subject, and tends to adhere more strongly to human skin, thus providing more effective compressive forces, Further, net growth of the animal subject during the observation period, although addressed in the data analysis, may still affect the normalized results. Such "net growth" effects would not typically be present in mature human patients, so the actual skin shrinkage may be greater and associated directional differences maybe greater.

SUMMARY

It will thus be appreciated that those skilled in the art will be able to devise numerous systems, arrangements and methods which, although not explicitly shown or described herein, embody the principles of the disclosure and are thus within the spirit and scope of the present disclosure. In addition, all publications, patents, and patent applications referenced herein are incorporated herein by reference in their entireties.

The invention claimed is:

1. A system for producing a cosmetic effect in skin tissue, the system comprising:
a plurality of round hollow coring needles configured to form a plurality of holes in a treatment region of the skin tissue;
a skin compression arrangement configured to produce and maintain a compressive stress over at least one portion of the treatment region after the plurality of holes are formed; and
a handpiece having a lower surface configured to be placed against the skin tissue in the treatment region,
wherein the plurality of round hollow coring needles are affixed to a substrate and configured to be movable relative to and through the lower surface of the handpiece, including being retractable wherein distal ends of the plurality of round hollow coring needles are positioned above the lower surface and fully within the handpiece.

2. The system of claim 1, wherein the system is configured to generate holes in the treatment region that extend from a surface of the skin tissue into a dermal layer of the skin tissue and remove skin tissue at an areal fraction of the treatment region between about 5% and 50%.

3. The system of claim 2, wherein at least one of the plurality of round hollow coring needles is structured to form a hole that extends from the surface of the skin tissue through the entire dermal layer of the skin tissue in the treatment region.

4. The system of claim 2, wherein the plurality of round hollow coring needles includes a number of round hollow coring needles between 2 and 50.

5. The system of claim 4, wherein the areal fraction of skin tissue to be removed from the treatment region is determined by at least one of the number of round hollow coring needles included in the plurality of round hollow coring needles or inner diameters of the plurality of round hollow coring needles.

6. The system of claim 1, wherein at least one round hollow coring needle of the plurality of round hollow coring needles has an inner diameter between about 0.2 mm and about 0.7 mm.

7. The system of claim 1, wherein the plurality of round hollow coring needles and the substrate are provided as a single unit that is configured to be removably attachable to the handpiece.

8. The system of claim 7, further comprising a plurality of single units including a first single unit and a second single unit, wherein the first single unit is configured to remove skin tissue at an areal fraction of the treatment region greater than the second single unit.

9. The system of claim 1, further comprising an actuator handle, wherein the actuator handle is configured to move the plurality of round hollow core needles and the substrate relative to the lower surface of the handpiece.

10. The system of claim 9, wherein the actuator handle is configured to withdraw the plurality of round hollow coring needles from the skin tissue when activated.

11. A system for producing a cosmetic effect in skin tissue, the system comprising:
a handpiece having a lower surface configured to be placed against the skin tissue in a treatment region; and
a plurality of single units, each single unit including a plurality of round hollow coring needles affixed to a substrate and configured to be removably coupled to the handpiece and form a plurality of holes in a treatment region of the skin tissue, and
wherein the plurality of round hollow coring needles of each single unit is configured to be movable relative to and through the lower surface of the handpiece, including being retractable wherein the plurality of round hollow coring needles are positioned fully within the handpiece.

12. The system of claim 11, wherein the plurality of round hollow coring needles on each single unit of the plurality of single units includes a number of round hollow coring needles between 2 and 50.

13. The system of claim 12, wherein the plurality of single units includes a first single unit and a second single unit, and
wherein at least one of the number of round hollow coring needles in the first single unit is greater or less than the number of round hollow coring needles in the second single unit or an average of the inner diameters of the plurality of round hollow coring needles in the first single unit is larger or smaller than an average of the inner diameters of the plurality of round hollow coring needles in the second single unit.

14. The system of claim 11, wherein at least one round hollow coring needle of the plurality of round hollow coring needles has an inner diameter between about 0.2 mm and about 0.7 mm.

15. The system of claim 11, further comprising an actuator handle, wherein the actuator handle is configured to move a single unit of the plurality of single units coupled to the handpiece relative to the handpiece.

16. The system of claim 11, wherein the system is configured to generate holes in the treatment region that extend from a surface of the skin tissue into a dermal layer of the skin tissue and remove skin tissue at an areal fraction of the treatment region between about 5% and 50%.

17. A system for producing a cosmetic effect in skin tissue, the system comprising:
- a handpiece having a lower surface configured to be placed against the skin tissue in a treatment region; and
- a plurality of round hollow coring needles affixed to a substrate and configured to be removably coupled to the handpiece and form a plurality of holes in a treatment region of the skin tissue; and
- an actuator handle configured to move the plurality of round hole coring needles and the substrate relative to and through the lower surface of the handpiece, including being retractable wherein the plurality of round hollow coring needles are positioned fully within the handpiece.

18. The system of claim 17, wherein the actuator handle is further configured to activate a skin compression arrangement that is configured to produce and maintain a compressive stress over at least one portion of the treatment region after the plurality holes are formed.

19. The system of claim 17, wherein at least one round hollow coring needle of the plurality of round hollow coring needles has an inner diameter between about 0.2 mm and about 0.7 mm.

20. The system of claim 17, wherein the system is configured to generate holes in the treatment region that extend from a surface of the skin tissue into a dermal layer of the skin tissue and remove skin tissue at an areal fraction of the treatment region between about 5% and 50%.

* * * * *